United States Patent
Pettinato

(10) Patent No.: US 8,526,571 B2
(45) Date of Patent: Sep. 3, 2013

(54) AIR BEARING DYNAMIC Z-AXIS BALANCING

(75) Inventor: Jeremy D. Pettinato, Cleveland, OH (US)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 12/993,966

(22) PCT Filed: May 29, 2009

(86) PCT No.: PCT/IB2009/052281
§ 371 (c)(1),
(2), (4) Date: Nov. 22, 2010

(87) PCT Pub. No.: WO2009/147604
PCT Pub. Date: Dec. 10, 2009

(65) Prior Publication Data
US 2011/0062354 A1  Mar. 17, 2011

Related U.S. Application Data

(60) Provisional application No. 61/058,238, filed on Jun. 3, 2008.

(51) Int. Cl.
*G01N 23/00* (2006.01)
(52) U.S. Cl.
USPC ............................................. 378/4; 378/197
(58) Field of Classification Search
USPC ........................ 378/4–20, 197–198
See application file for complete search history.

(56) References Cited

U.S. PATENT DOCUMENTS

| | | | |
|---|---|---|---|
| 6,276,145 B1 | 8/2001 | Sharpless et al. | |
| 6,404,845 B1 | 6/2002 | Sharpless et al. | |
| 6,412,345 B1 | 7/2002 | Murray et al. | |
| 6,550,317 B2 | 4/2003 | Steinlage et al. | |
| 6,590,960 B2 | 7/2003 | Kroener et al. | |
| 6,890,100 B2 | 5/2005 | Reznicek et al. | |
| 7,236,855 B2 | 6/2007 | Danz et al. | |
| 2002/0114424 A1 | 8/2002 | Kroener et al. | |
| 2003/0046987 A1 | 3/2003 | Steinlage et al. | |
| 2004/0062356 A1* | 4/2004 | Brunnett | 378/196 |
| 2005/0013403 A1* | 1/2005 | Reznicek et al. | 378/15 |
| 2006/0229845 A1 | 10/2006 | Buttner | |
| 2007/0041488 A1 | 2/2007 | Hoheisel et al. | |

FOREIGN PATENT DOCUMENTS

| | | |
|---|---|---|
| EP | 1095620 A1 | 5/2001 |
| JP | 2005257030 A | 9/2005 |

* cited by examiner

*Primary Examiner* — Hoon Song

(57) ABSTRACT

A medical imaging system (100) includes a stationary gantry (102) and a rotating gantry (104) that rotates around an examination region (108) about a z-axis. An air bearing (106) rotatably couples the rotating gantry (104) to the stationary gantry (102). A radiation source (110) is affixed to the rotating gantry (104) and rotates with the rotating gantry (104) and emits radiation that traverses the examination region. A detector array (112) is affixed to the rotating gantry (104) on an opposite side of the examination region with respect to the radiation source (110) and detects radiation traversing the examination region (108). A dynamic z-axis imbalance determination system (116) determines an imbalance of the rotating gantry (104) in the z-axis direction directly from the air bearing (106), and the determined imbalance is used to position a balance mass (114) affixed to the rotating gantry (104) in the z-axis direction, thereby balancing the rotating gantry (104) along the z-axis.

12 Claims, 4 Drawing Sheets

US 8,526,571 B2

AIR BEARING DYNAMIC Z-AXIS BALANCING

CROSS REFERENCE TO RELATED APPLICATIONS

This application claims the benefit of U.S. provisional application Ser. No. 61/058,238 filed Jun. 3, 2008, which is incorporated herein by reference.

The present application relates to medical imaging systems, and finds particular application to computed tomography (CT). However, it is also amenable to other medical imaging applications and to non-medical imaging applications.

A computed tomography (CT) scanner includes a stationary gantry and a rotating gantry that rotates, with respect to the stationary gantry, around an examination region about a longitudinal or z-axis. The rotating gantry is supported on the stationary gantry via a bearing such as a ball bearing. A radiation source and a radiation sensitive detector array are affixed to the rotating gantry on opposite sides of the examination region. Other components such as a heat exchanger, a collimator, a power module, etc. are also affixed to the rotating gantry. The radiation source emits radiation that traverses the examination region and illuminates the detector array, which generates a signal indicative of the radiation. A reconstructor reconstructs the signal to generate volumetric image data.

In one configuration, the radiation source, the detector array and various other components cantilever from the rotating gantry. With such a configuration, each cantilevered component is associated with a moment that tends to cause the component to rotate about the end affixed to the rotating gantry. Generally, the moment is a function of the length of the component in the z-axis direction and the forces (gravitational and radial g forces) acting upon the component, the forces being a function of the mass of the component and the angular acceleration. As a consequence, the distribution of the components about the rotating gantry may result in a dynamic imbalance, or tendency for the rotating gantry and the bearing to wobble or distort in the z-axis direction. Generally, the distortion increases with rotational speed.

Dynamic z-axis balancing is a technique in which balance masses are mounted to the rotating gantry to balance (or reduce the imbalance) in the z-axis direction. For dynamic z-axis balancing, parameters such as the mass of each component and the square of the distance that the component extends from the rotating gantry in the z-axis direction are determined. The square of the distance arises from the forcing function and the moment arm dimension. The forcing function for dynamic balancing is due to the rotation of the system and is oriented in the radial direction. Dynamic z-axis imbalance may also be thought of as two plane imbalance, and is representative of correction masses needed in the two planes in order to eliminate the imbalance.

With a scanner in which the rotating gantry is supported by the stationary gantry via ball bearings, an accelerometer or the like has been used to measure z-axis imbalance. By way of example, an accelerometer has been mounted to a designated region in the stationary gantry to measure vibrations associated with an unbalanced rotating gantry that have translated to the stationary gantry. The accelerometer produces an electrical signal indicative of the imbalance, and the signal is used to determine an appropriate balance mass and balance mass z-axis position to counter the imbalance. However, continuing advances in scanner related technologies are leading to scanners that employ other types of bearings for supporting the rotating gantry on the stationary gantry. Although accelerometers mounted to the stationary gantry are well suited for ball bearing based systems, they may not be very well suited for other types of bearings.

Aspects of the present application address the above-referenced matters and others.

According to one aspect, a medical imaging includes a stationary gantry and a rotating gantry that rotates around an examination region about a z-axis. An air bearing rotatably couples the rotating gantry to the stationary gantry. A radiation source is affixed to the rotating gantry and rotates with the rotating gantry and emits radiation that traverses the examination region. A detector array is affixed to the rotating gantry on an opposite side of the examination region with respect to the radiation source and detects radiation traversing the examination region. A dynamic z-axis imbalance determination system determines an imbalance of the rotating gantry in the z-axis direction directly from the air bearing, and the determined imbalance is used to position a balance mass affixed to the rotating gantry in the z-axis direction, thereby balancing the rotating gantry along the z-axis.

According to another aspect, a method includes measuring a z-axis imbalance of a rotating gantry of a medical imaging system. The rotating gantry rotates via an air bearing coupled to a stationary gantry and the z-axis imbalance is measured at the air bearing. The method further includes determining a z-axis position of a balance mass to counter the measured z-axis imbalance, and positioning the balance mass in accordance with the determined position, thereby balancing the rotating gantry in the z-axis direction.

According to another aspect, a method includes detaching a bearing block of an air bearing from a bearing block mounting location of a stationary gantry of a medical imaging system, attaching a dynamic z-axis imbalance determination system to the location, and dynamically balancing a rotating gantry of the medical imaging system in a z-axis direction, wherein the rotating gantry is rotatably coupled to the stationary gantry via the air bearing and vibrational loads translating from the rotating gantry to the bearing are measured by the dynamic z-axis imbalance determination system directly at the bearing.

According to another aspect, a dynamic z-axis imbalance determination system for an imaging system includes a mounting bracket configured to mount to a stationary portion of the imaging system, a bearing block pad, a load measurement device coupled to and disposed between the mounting bracket and the bearing block pad, and a bearing block of an air bearing, wherein the bearing block is coupled to the bearing block pad on a side opposite the load measurement device.

The invention may take form in various components and arrangements of components, and in various steps and arrangements of steps. The drawings are only for purposes of illustrating the preferred embodiments and are not to be construed as limiting the invention.

Figure 1:
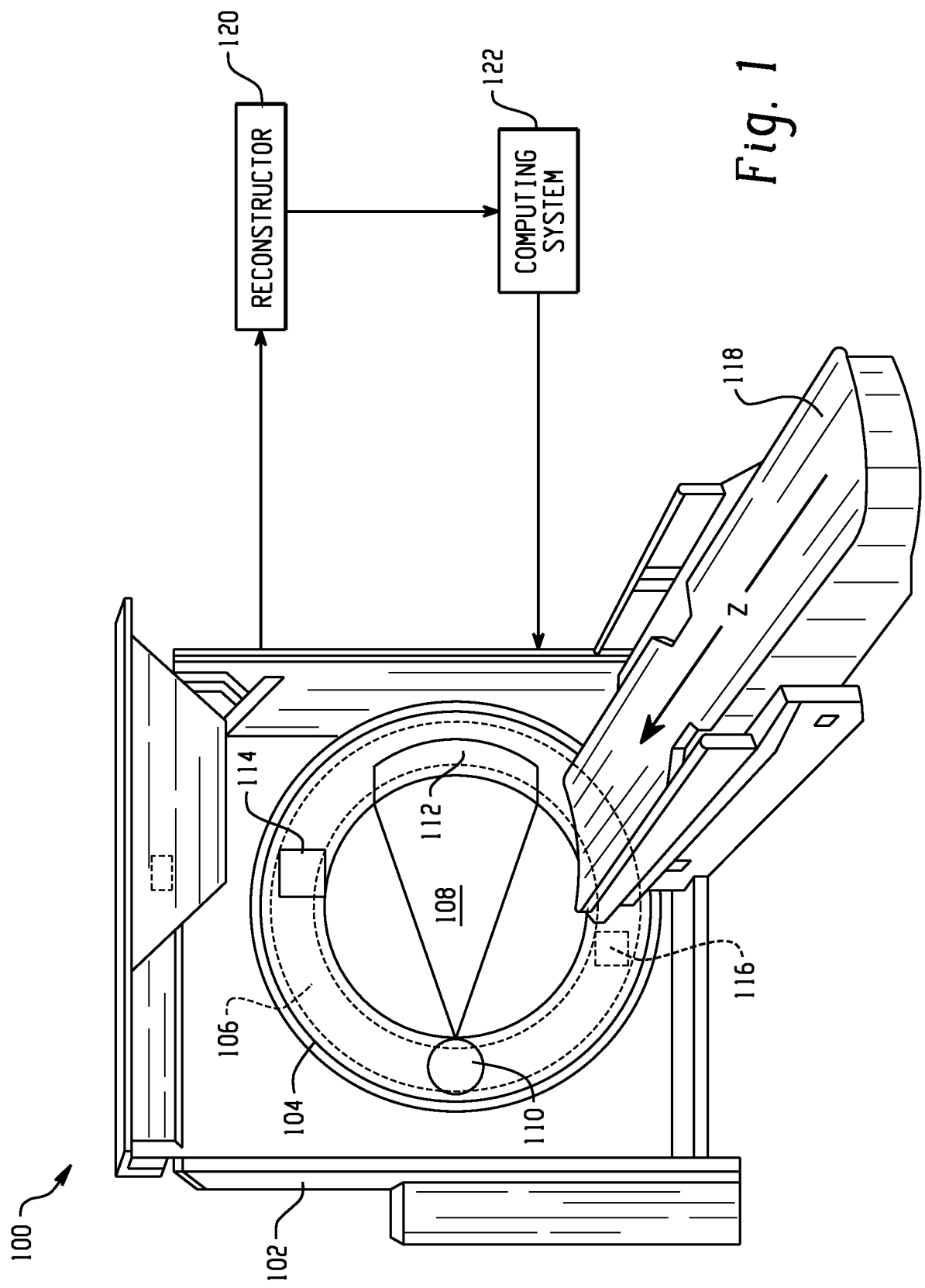
FIG. 1 illustrates an example medical imaging system.

Initially referring to FIG. 1, a computed tomography (CT) scanner 100 includes a stationary gantry 102 and a rotating gantry 104. The rotating gantry 104 is rotatably supported by the stationary gantry 102 via an air bearing 106. An example of a suitable air bearing is described in U.S. Pat. No. 6,276,145, Ser. No. 09/428,431, filed Oct. 27, 1999, and entitled "Aerostatic CT suspension."

The rotating gantry 104 rotates, with respect to the stationary gantry 102, around an examination region 108 about a longitudinal or z-axis. In the illustrated example, the rotating gantry 104 is configured to rotate at rotational speeds up to 300 revolutions per minute (RPM), for example, at about 220 RPM for a cardiac based application. The rotating gantry 104 is also generally stiff, with a first natural frequency of about 20 hertz (Hz).

As a result of the stiffness of the rotating gantry 104, vibrational loads translating from components affixed to the rotating gantry 104 to the bearing 106 tend to substantially dampen out before (if at all) translating to the stationary gantry 102, and thereby are much stronger at the bearing 106 relative to regions on the stationary gantry 102.

A radiation source 110, such as an x-ray tube, is affixed to and cantilevers from the rotating gantry 104. The radiation source 110 emits radiation that traverses the examination region 108. In this example, the emitted radiation is collimated by a source collimator affixed to the rotating gantry 104 to produce a generally conically shaped radiation beam. In other embodiments, the collimator collimates the radiation to produce a generally fan or other shaped beam.

A radiation sensitive detector array 112 cantilevers from and is affixed to the rotating gantry 104 such that it subtends an angular arc on a side of the examination region 108 opposite the radiation source 110. The detector array 112 includes one or more rows of radiation sensitive detector elements that extend in the z-axis direction and that detect radiation that traverses the examination region 108.

Other components such as a heat exchanger, a collimator, a power module, etc., although not shown, are also affixed to and cantilever from the rotating gantry 104.

Balance masses 114 are selectively affixed to the rotating gantry 104 to balance the weight distribution of the components over the rotating gantry 104 and counter any moments or torques due to forces acting upon the components, which may cause the bearing 106 to wobble or distort when rotating. The balance masses 114 generally are added at multiple different designated locations on the rotating gantry 104 in the x-y plane, and are adjustable along the z-axis to balance the rotating gantry 104 in the z-axis direction. For sake of clarity, in this non-limiting example only one set of balance masses 114 at one arbitrary location are shown.

The stationary gantry 102 is configured so that it does not tilt for scanning purposes, rendering the stationary gantry 102 generally stiffer relative to a configuration in which the stationary gantry 102 tilts for scanning purposes. Like the rotating gantry 104, the stationary gantry has a first natural frequency of about 20 hertz (Hz).

A dynamic z-axis imbalance determination system 116 generates a signal indicative of an imbalance of the rotating gantry 104 along the z-axis as the rotating gantry 104 rotates. As discussed above, an imbalance may occur due to the distribution of the components (masses) cantilevering from the rotating gantry 104 and the gravitational and radial g forces acting upon the components at the various rotational speed. Note that as the bearing 106 is an air bearing, the rotating gantry 104 generally is always in a free floating state.

As described in greater detail below, in one embodiment the dynamic z-axis imbalance determination system 116 includes a vibration measurement system such as a load cell or the like coupled to, integrated with, and in operative communication with the bearing 106. As such, the dynamic z-axis imbalance determination system 116 generally does not require additional space for mounting. Rather, the dynamic z-axis imbalance determination system 116 occupies substantially the same space that would otherwise be occupied by the bearing 106 and the support structure for the bearing. This is unlike conventional techniques in which accelerometers or the like are attached to the stationary gantry 102, in addition to the other components, to dedicated areas on the stationary gantry 102.

Being coupled to the bearing 106, the dynamic z-axis imbalance determination system 116 measures vibrational information indicative of the z-axis imbalance of the rotating gantry 104 directly from the bearing 106, where the vibrational level is much stronger relative to the stationary gantry 102 due, at least in part, to the stiffness of the rotating gantry 104 and the dampening of the vibrational loads thereby. By way of example, when rotating the rotating gantry 104 at about 220 RPM (3.67 Hz), most of the residual vibrations dampen out before translating to the stationary gantry 102.

A patient support 118, such as a couch, supports a patient in the examination region 108. The patient support 118 is movable along the z-axis in coordination with the rotation of the rotating gantry 104 to facilitate helical, axial, or other desired scanning trajectories.

A reconstructor 120 reconstructs projection data from the detectors to generate volumetric data indicative of the examination region and any object dispose therein during scanning.

A general purpose computing system serves as an operator console 122. The operator console 122 includes human readable output devices such as a display and/or printer and input devices such as a keyboard and/or mouse. Software resident on the console 122 allows the operator to control operation of the system 100, including during calibration, for example, when performing dynamic z-axis balancing. During such a calibration, the software enables a technician to determine appropriate z-axis counter balance mass positioning so as to mitigate rotating gantry 104 z-axis distortions or wobble.

Figure 4:
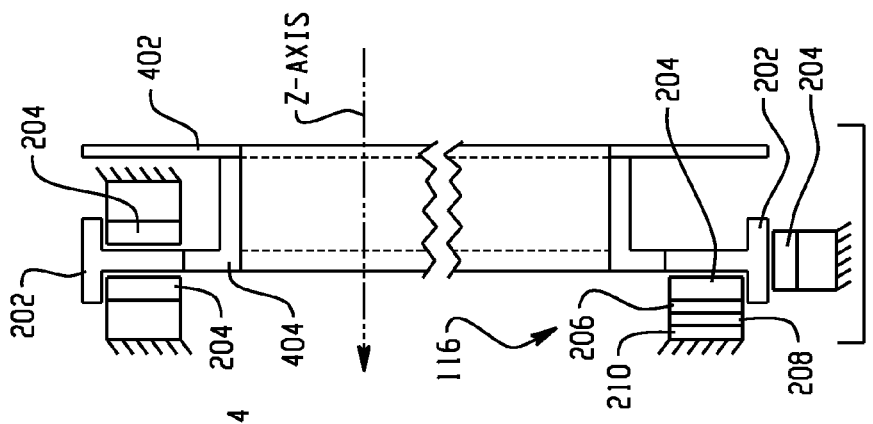
FIG. 4 illustrates a side view of the air bearing along with the rotor and a dynamic z-axis imbalance determination system.
Figure 3:
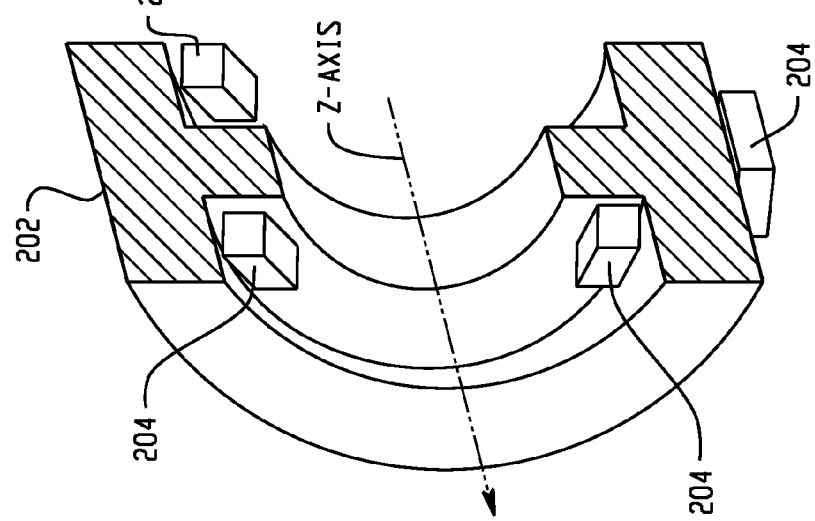
FIG. 3 illustrates a perspective view of the air bearing, including the annular portion and the bearing blocks.
Figure 2:
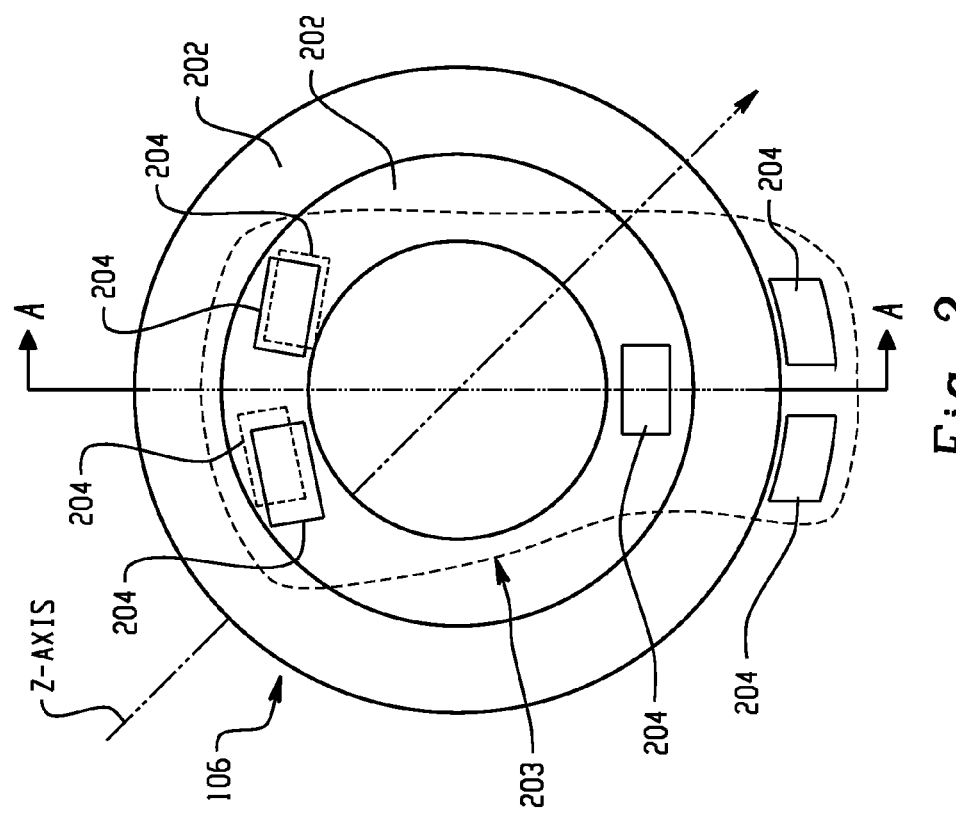
FIG. 2 illustrates a back view of an air bearing, including an annular portion and bearing blocks.

FIGS. 2, 3, and 4 show various views of the bearing 106. FIG. 2 shows a view looking into the bearing 106 from behind the scanner 100, FIG. 3 shows a perspective view looking into cross section A-A of FIG. 2, and FIG. 4 shows a side view looking into cross section A-A of FIG. 2. FIG. 4 also shows the rotor 402, an example connection 404 between the air bearing 106 and the rotor 402, and the dynamic imbalance determination system 116.

Initially referring to FIG. 2, the bearing 106 includes a first portion 202 with a generally annular shaped, two-tiered ring. As shown in FIGS. 3 and 4, each side of the first portion 202 includes two-tiers, and the tiers form a "T" shaped first portion 202. Referring to FIGS. 2, 3, and 4, the bearing 106 also includes a second portion 203, which includes one or more bearing blocks 204, each being placed at different locations with respect to the first portion 202. In the illustrated example, there are seven bearing blocks 204, two located on a front side of the bearing 106, three located at a backside of the bearing 106, and two located under the bearing 106. The illustrated number and location are for explanatory purposes, and not limiting. An air gap such as a three (3) micron air gap exists between each of the bearing blocks 204 and first portion 202.

As noted above, in one embodiment the dynamic z-axis imbalance determination system 116 is integrated with the bearing 106. As shown in FIG. 4, the dynamic z-axis imbalance determination system 116 is integrated with at least one of the bearing blocks 204 and includes, in addition to the bearing block 204, a bearing block mounting pad 206, a vibrational load measurement device 208, and a mounting bracket 210.

Figure 5:
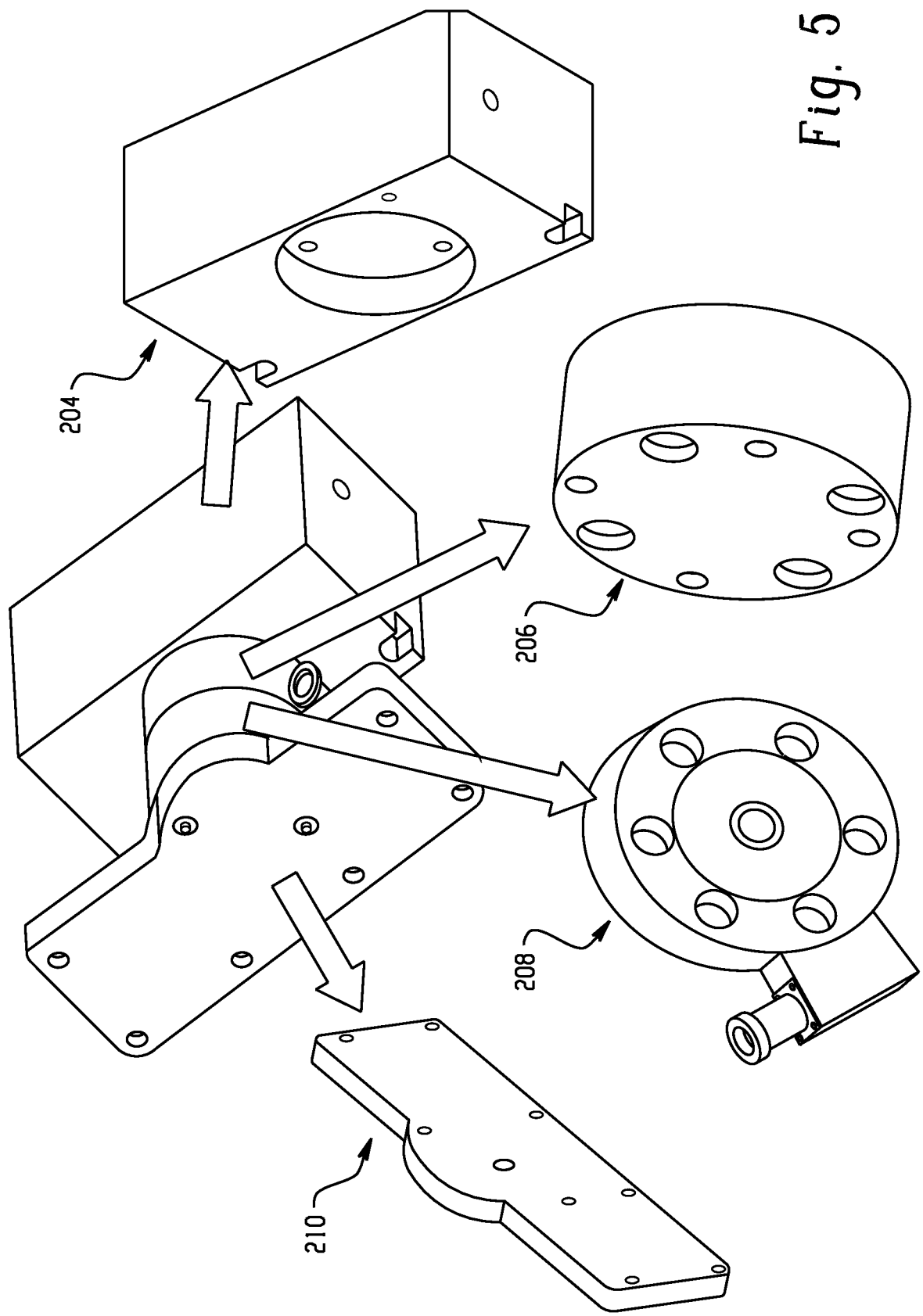
FIG. 5 illustrates an example dynamic imbalance determination system.

This is further illustrated in FIG. 5, which shows the bearing block 204 affixed to the bearing block mounting pad 206, which is affixed to the vibrational load measurement device 208 (which is a load cell in this example), which is affixed to the mounting bracket 210. The mounting bracket 210 is affixed to the stationary gantry 102. Various types of fastening mechanisms can be used to fasten the components together. Non-limiting examples include nuts and bolts, screws, rivets, welds, etc.

Variations are contemplated.

In the example above, the dynamic imbalance determination system 116 is shows as part of the scanner 100. In another embodiment, the dynamic imbalance determination system 116 is removably installable. By way of example, a technician can temporarily remove one of the bearing blocks 204 from the stationary frame 102 and replace it with the dynamic z-axis imbalance determination system 116. After dynamically balancing the rotating gantry 104 along the z-axis, the dynamic imbalance determination system 116 can be removed and the bearing block 204 can be re-attached to the scanner 100.

In another example, the output of the dynamic imbalance determination system 116 is continuously or intermittently feedback to a balancing component that automatically positions the balance masses along the z-axis, for example, it automatically moves trim weights in the z-axis direction, to maintain system balance.

In another embodiment, the mounting bracket 210 is part of the stationary gantry 102, and the other portions of the dynamic z-axis balancing system are attached thereto as described above.

In another embodiment, more than one dynamic imbalance determination system 116 is concurrently installed on the scanner 100.

In another embodiment, the scanner 100 is configured to tilt.

Figure 6:
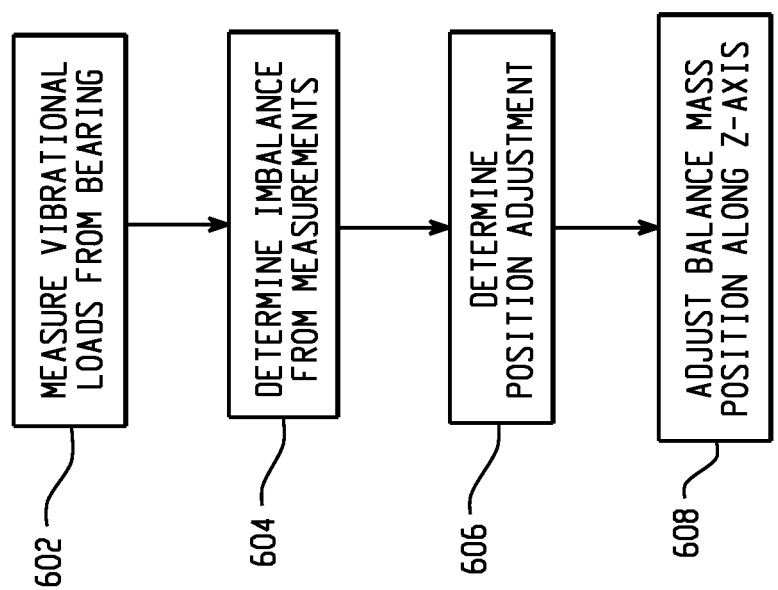
FIG. 6 illustrates an example of a method for calibrating for dynamic z-axis imbalance.

FIG. 6 illustrates a method for dynamic z-axis balancing of the rotating gantry 104 of an air bearing based system. At 602, vibrational loads corresponding to rotating masses on the rotating gantry 104 are measured directly at the bearing 106. At 604, the measurements are used to determine an imbalance, if any. At 606, a z-axis position adjustment of a balance mass is determined. At 608, the balance mass 114 is accordingly positioned, if at all, along the z-axis. Where the system is already balanced or the imbalance is below a pre-set balance threshold, the current balance mass 114 need not be adjusted. Any adjustment can be done automatically by the system 100 or manually by a technician. These steps are repeatable.

Figure 7:
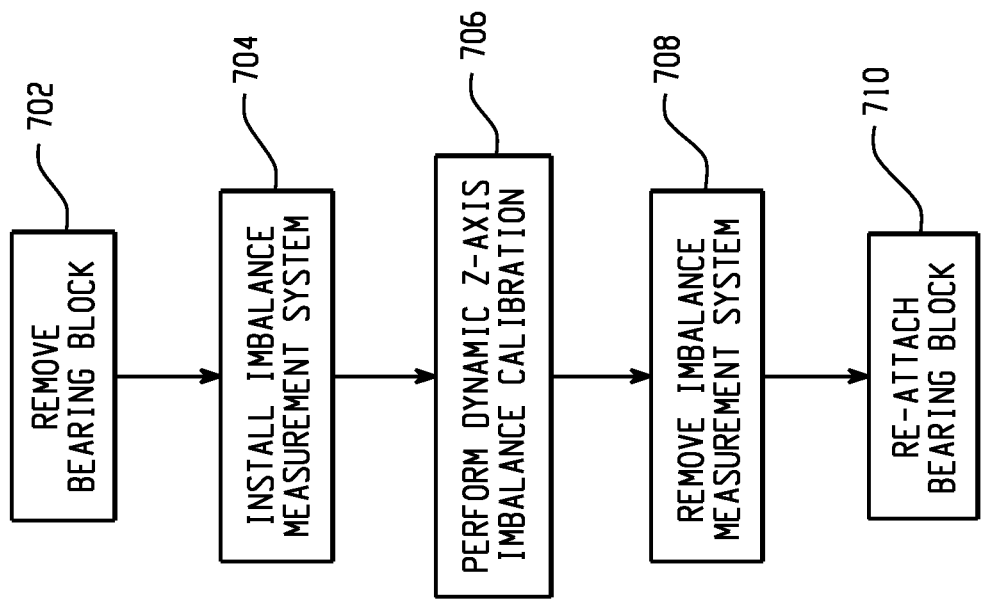
FIG. 7 illustrates an example of a method for using the dynamic z-axis imbalance determination system.

FIG. 7 illustrates a method for dynamic z-axis balancing of the rotating gantry 104 of an air bearing based system. At 702, one of the bearing blocks 204 is removed from the bearing 106. At 704, the imbalance determination system 116 is removeably affixed to the bearing 106. At 706, a dynamic z-axis calibration procedure is performed for the rotating gantry 104. At 708, after the dynamic z-axis calibration procedure, the imbalance determination system 116 is removed from the rotating gantry 104. At 710, the bearing block 204 is re-attached to the rotating gantry 104.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described various embodiments, we claim:

1. An imaging system, comprising:
   a stationary gantry;
   a rotating gantry that rotates around an examination region about a z-axis;
   an air bearing that rotatably couples the rotating gantry to the stationary gantry;
   a radiation source affixed to the rotating gantry, wherein the radiation source rotates with the rotating gantry and emits radiation that traverses the examination region;
   a detector array affixed to the rotating gantry on an opposite side of the examination region with respect to the radiation source, wherein the detector array detects radiation traversing the examination region;
   a balance mass affixed to the rotating gantry;
   a dynamic z-axis imbalance determination system that determines an imbalance of the rotating gantry in the z-axis direction directly from the air bearing, wherein the determination system uses the determined imbalance to position a balance mass affixed to the rotating gantry in the z-axis direction, thereby balancing the rotating gantry along the z-axis;
   a bearing block pad;
   a vibrational load measurement device; and
   a mounting bracket, wherein the mounting bracket is affixed to the stationary gantry, the vibrational load measurement device is affixed to the mounting bracket, the bearing block pad is affixed to the vibrational load measurement device, and the bearing block is affixed to the bearing block pad.

2. The system of claim 1, wherein the vibrational load measurement device measures vibrational loads that translate from the rotating gantry to the air bearing.

3. The system of claim 2, wherein the vibrational load measurement device is a load cell.

4. The system of claim 2, wherein the radiation source and the detector array cantilever from the rotating gantry, and the vibrational loads are due to gravitational and radial g forces acting on the detector array and the rotating gantry as the rotating gantry rotates.

5. The system of claim 1, wherein the air bearing includes:
   a first portion affixed to the rotating gantry; and
   a second portion affixed to the stationary gantry, wherein the dynamic z-axis imbalance determination system is affixed to the second portion.

6. The system of claim 5 wherein the second portion includes one or more bearing blocks and the dynamic z-axis imbalance determination system is integrated with one of the one or more bearing blocks.

7. The system of claim 1, wherein
   the vibrational load measurement device is directly affixed to the mounting bracket.

8. The system of claim 1, wherein the determination system automatically positions the balance mass.

9. The system of claim 1, wherein substantially all of the vibrational loads translating to the bearing from the rotating gantry dampen out before translating to the stationary gantry.

10. The system of claim 1, wherein the dynamic z-axis imbalance determination system occupies about the same amount of space as a bearing block and bearing block support structure of the bearing.

11. The system of claim 1, wherein the dynamic z-axis imbalance determination system is removably installable on the stationary gantry when performing a dynamic z-axis calibration.

12. The system of claim 1, wherein the dynamic z-axis imbalance determination system is swappable with a bearing block of the air bearing.

* * * * *